United States Patent
Barasch

(10) Patent No.: US 10,310,805 B2
(45) Date of Patent: Jun. 4, 2019

(54) SYNCHRONIZED SOUND EFFECTS FOR SEXUAL ACTIVITY

(71) Applicant: Maxine Lynn Barasch, Albany, NY (US)

(72) Inventor: Maxine Lynn Barasch, Albany, NY (US)

( * ) Notice: Subject to any disclaimer, the term of this patent is extended or adjusted under 35 U.S.C. 154(b) by 4 days.

(21) Appl. No.: 15/402,675

(22) Filed: Jan. 10, 2017

(65) Prior Publication Data

US 2017/0199720 A1 Jul. 13, 2017

Related U.S. Application Data

(60) Provisional application No. 62/277,156, filed on Jan. 11, 2016.

(51) Int. Cl.
  *G06F 17/00* (2019.01)
  *G06F 3/16* (2006.01)
  *H04W 4/80* (2018.01)
  *A61H 19/00* (2006.01)
  *A61M 21/02* (2006.01)
  *A61M 21/00* (2006.01)

(52) U.S. Cl.
  CPC .............. *G06F 3/165* (2013.01); *A61H 19/32* (2013.01); *A61H 19/50* (2013.01); *A61M 21/02* (2013.01); *H04W 4/80* (2018.02); *A61H 2201/0188* (2013.01); *A61H 2201/165* (2013.01); *A61H 2201/1609* (2013.01); *A61H 2201/1628* (2013.01); *A61H 2201/50* (2013.01); *A61H 2201/5043* (2013.01); *A61H 2201/5048* (2013.01); *A61H 2201/5058* (2013.01); *A61H 2201/5097* (2013.01); *A61M 2021/0027* (2013.01); *A61M 2021/0044* (2013.01); *A61M 2205/3313* (2013.01); *A61M 2205/3317* (2013.01); *A61M 2210/1475* (2013.01); *A61M 2210/167* (2013.01)

(58) Field of Classification Search
  CPC .......... A61H 19/00; A61H 19/50; G06F 3/165
  See application file for complete search history.

(56) References Cited

U.S. PATENT DOCUMENTS

| | | | | |
|---|---|---|---|---|
| 2006/0079732 | A1* | 4/2006 | Blumenthal | A61H 19/00 600/38 |
| 2012/0214644 | A1* | 8/2012 | Sasaki | G06F 19/3481 482/3 |
| 2016/0173982 | A1* | 6/2016 | Anderson | H04R 3/00 381/119 |

* cited by examiner

*Primary Examiner* — Joseph Saunders, Jr.
(74) *Attorney, Agent, or Firm* — Maxine L. Barasch; Keohane & D'Alessandro PLLC

(57) ABSTRACT

Embodiments of the present invention provide a system, method, and apparatus for enhancing a sexual intercourse experience. A first sensor is worn on a first person engaging in sexual intercourse with a second person. A second sensor is worn on the second person. The proximity of the first and second sensors is communicated to a sound module that outputs sound, music, and/or lights that are synchronized to the thrusting motion occurring during the sexual intercourse.

17 Claims, 16 Drawing Sheets

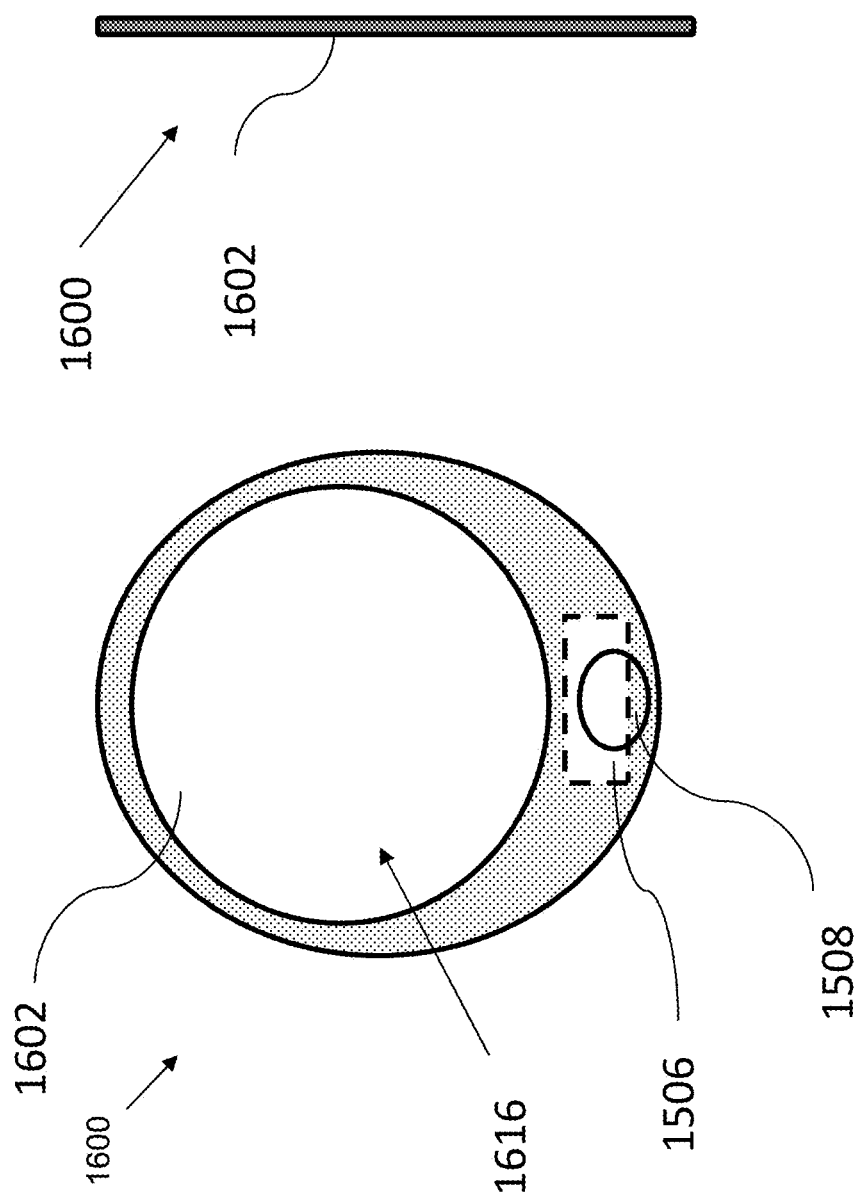

SYNCHRONIZED SOUND EFFECTS FOR SEXUAL ACTIVITY

CROSS-REFERENCE TO RELATED APPLICATION

The present patent document claims priority to, U.S. Provisional Patent Application No. 62/277,156 filed Jan. 11, 2016, the entire contents of which is incorporated herein by reference.

FIELD OF THE INVENTION

The present invention relates generally to an apparatus and system for use during sexual activity, and more particularly, to an apparatus and system for producing sound effects synchronized to sexual activity.

BACKGROUND

Human sexual activity is an important part of many relationships. Sexual activity can serve to heighten feelings of love and intimacy. It is therefore desirable to have an apparatus and system for increasing the excitement that is experienced during sexual activity.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

FIG. 16A shows a front view of a necklace in accordance with some embodiments of the invention.

FIG. 16B shows a side view of the necklace of FIG. 16A.

Figure 1:
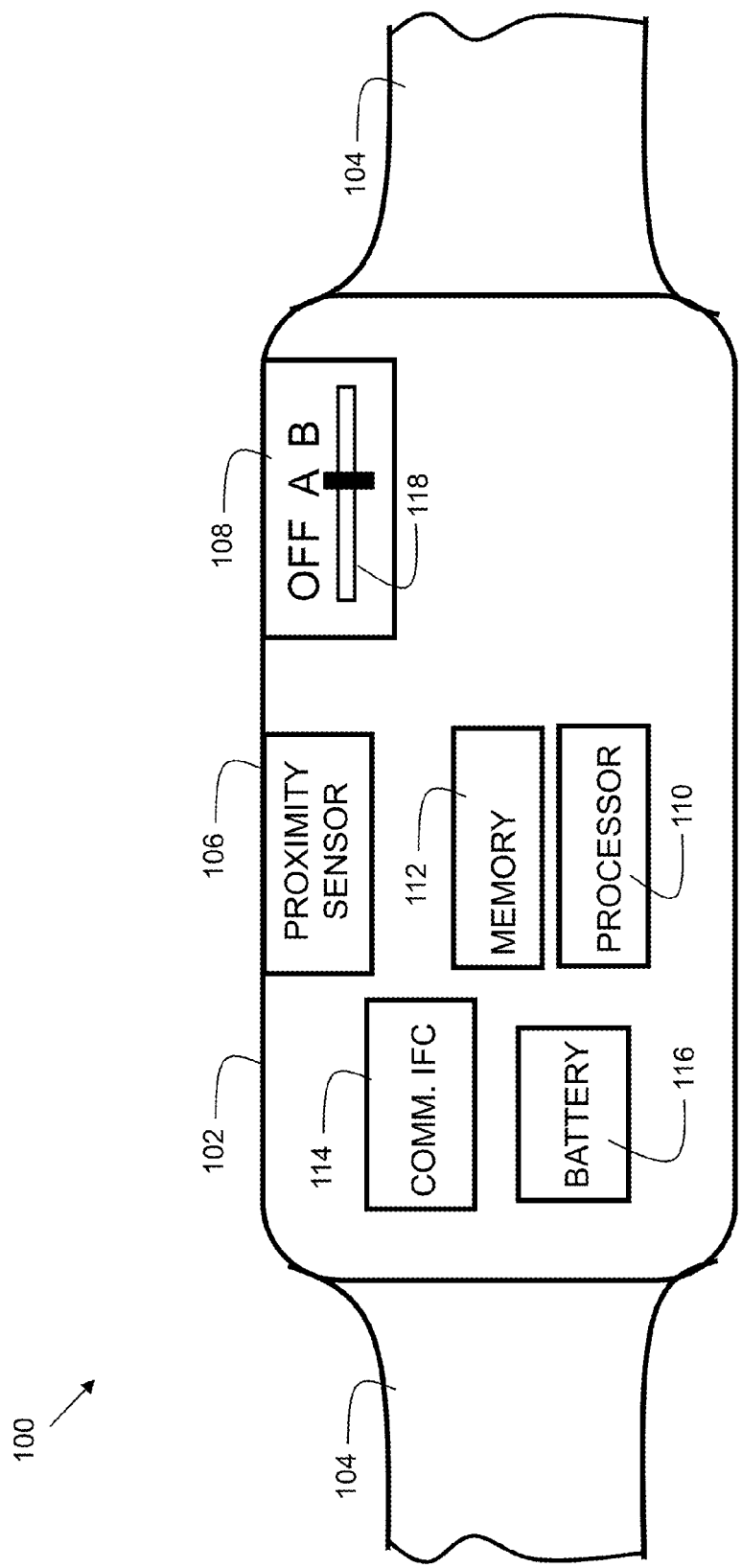
FIG. 1 shows a block diagram of a wearable relative position indicator in accordance with embodiments of the present invention.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements. Furthermore, certain elements in some of the figures may be omitted, or illustrated not-to-scale, for illustrative clarity.

DETAILED DESCRIPTION

Embodiments of the present invention provide a system, method, and apparatus for enhancing a sexual intercourse experience. A first sensor is worn on a first person engaging in sexual intercourse with a second person. A second sensor is worn on the second person. The proximity of the first and second sensors is communicated to a sound module that outputs sound, music, and/or lights that are synchronized to the thrusting motion occurring during the sexual intercourse.

Reference throughout this specification to "one embodiment," "an embodiment," "some embodiments," "in embodiments," or similar language means that a particular feature, structure, or characteristic described in connection with the embodiment is included in at least one embodiment of the present invention. Thus, appearances of the phrases "in one embodiment," "in an embodiment," "in some embodiments," "in embodiments," and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents. Reference will now be made in detail to the preferred embodiments of the invention.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, integers, steps, operations, elements, components, and/or groups thereof.

FIG. 1 shows a block diagram 100 of a wearable relative position indicator (WRPI) in accordance with embodiments of the present invention. WRPI 100 includes a housing 102, which may be comprised of plastic. Contained within housing 102 is a proximity sensor 106.

The proximity sensor 106 may be a magnetic based proximity sensor, infrared proximity sensor, laser proximity sensor, radio based proximity sensor, or any other suitable sensor type. WRPI 100 further comprises a processor 110, which is coupled to memory 112. Memory 112 contains instructions, that when executed by the processor, perform the functions of the WRPI 100. WRPI 100 further includes a battery 116 for providing power to the memory, processor, and other electronic components within the WRPI 100. In embodiments, the battery 116 may be a rechargeable battery that is recharged from a port such as a micro-USB port (not shown). In other embodiments, the battery may be charged via an inductive charging mechanism. WRPI 100 further includes a communication interface 114. The communications interface 114 includes a wireless communications transmitter. The communications interface 114 may include a Bluetooth™ interface, a frequency modulation (FM) radio, and/or an amplitude modulation (AM) radio. In the example of FIG. 1, the housing 102 is affixed to a belt 104 that is configured to be worn around the waist or torso of a user. WRPI 100 further includes controls 108 which may be disposed on the outside of housing 102. In embodiments, the controls 108 includes a slider switch 118 that enables the WRPI 100 to be turned off, or set to an A configuration, or a B configuration. These configurations are explained further in the following paragraphs. Note that the invention is not limited to inclusion of a belt. Any wearable apparatus is included within the scope of the invention. For example, WRPI could be worn as a necklace.

Figures 15A, 15B:
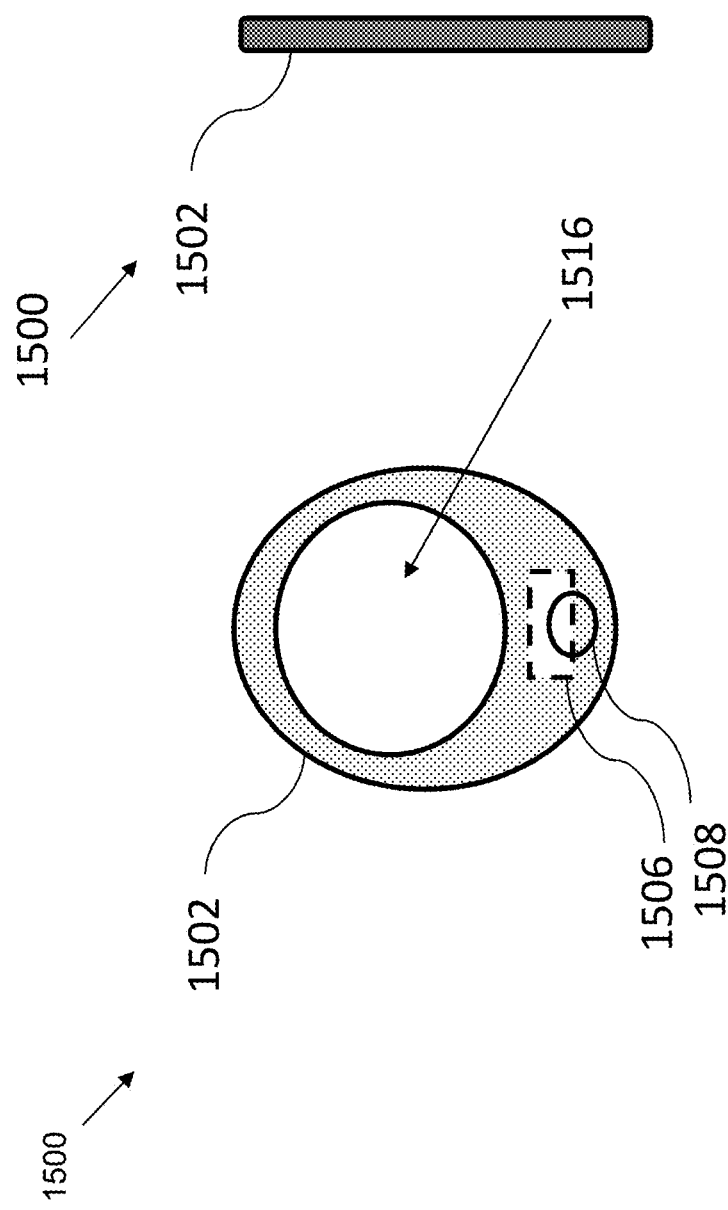
FIG. 15A shows a front view of a penis ring in accordance with some embodiments of the invention.
FIG. 15B shows a side view of FIG. 15A.

FIG. 15A shows a front view of a penis ring 1500 in accordance with some embodiments of the invention. FIG. 15B shows a side view of the ring 1500. In some embodiments, the components described in relation to the belt of FIG. 1 may instead be housed in a penis ring. Penis ring 1500 has a flexible ring 1502 for attachment to a penis and/or scrotum. The flexible ring 1502 has an insert hole 1504 through which a penis or scrotum is to be inserted and elastically constricted. The constriction holds the ring to the penis. The internal components of FIG. 1 are represented collectively in general at 1506. External controls are represented as 1508, and are substantially similar to those of FIG. 1.

FIG. 16A shows a front view of a necklace 1600 in accordance with some embodiments of the invention. FIG. 16B shows a side view of the necklace 1600. In some embodiments, the components described in relation to the belt of FIG. 1 may instead be housed in a necklace. Necklace 1600 has a band 1602 for wearing around a user's neck. The band 1603 has an insert hole 1604 through which a neck is to be inserted. Ideally, the bank would have a snug fit around the neck to keep sensor in place during use. The internal components of FIG. 1 are represented collectively in general at 1606. External controls are represented as 1608, and are substantially similar to those of FIG. 1.

It should be noted that any wearable apparatus including the elements of FIG. 1 is included within the scope of the invention. The invention is not limited to these examples. Note, in some embodiments, the device may be remote controlled by a remote control, a computer, or mobile application. Bluetooth™ or other suitable near field communication may be used. Accordingly, external controls may not be included in some embodiments.

Figure 2:
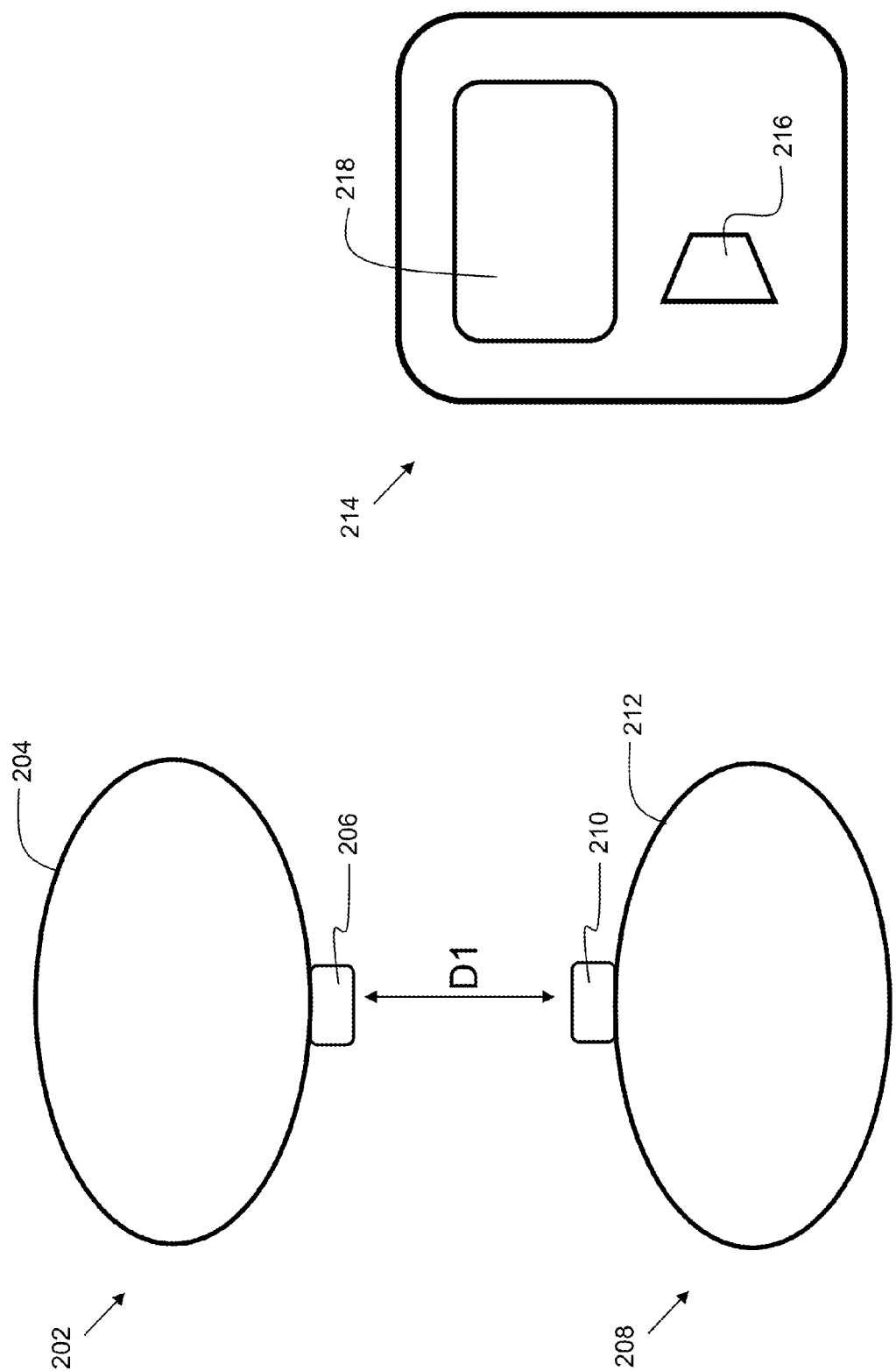
FIG. 2 shows a system with two relative position indicators and a sound module in a non-activated state.

FIG. 2 shows a system with two wearable relative position indicators and a sound module in a non-activated (non-proximal) state. WRPI 202 includes housing 206 (containing components as indicated in FIG. 1) attached to a belt 204. Similarly, WRPI 208 includes housing 210 (containing components as indicated in FIG. 1) attached to a belt 210. During use, WRPI 202 is worn by a first person, and WRPI 208 is worn by a second person. A sound module 214 is positioned nearby the two users. Typically, the sound module 214 may be located in the same room as the users, or within fifteen feet of the two users. The sound module 214 includes a speaker 216, and may further include a display 218. As shown, the two WRPI housings are separated by a distance D1.

Figure 3:
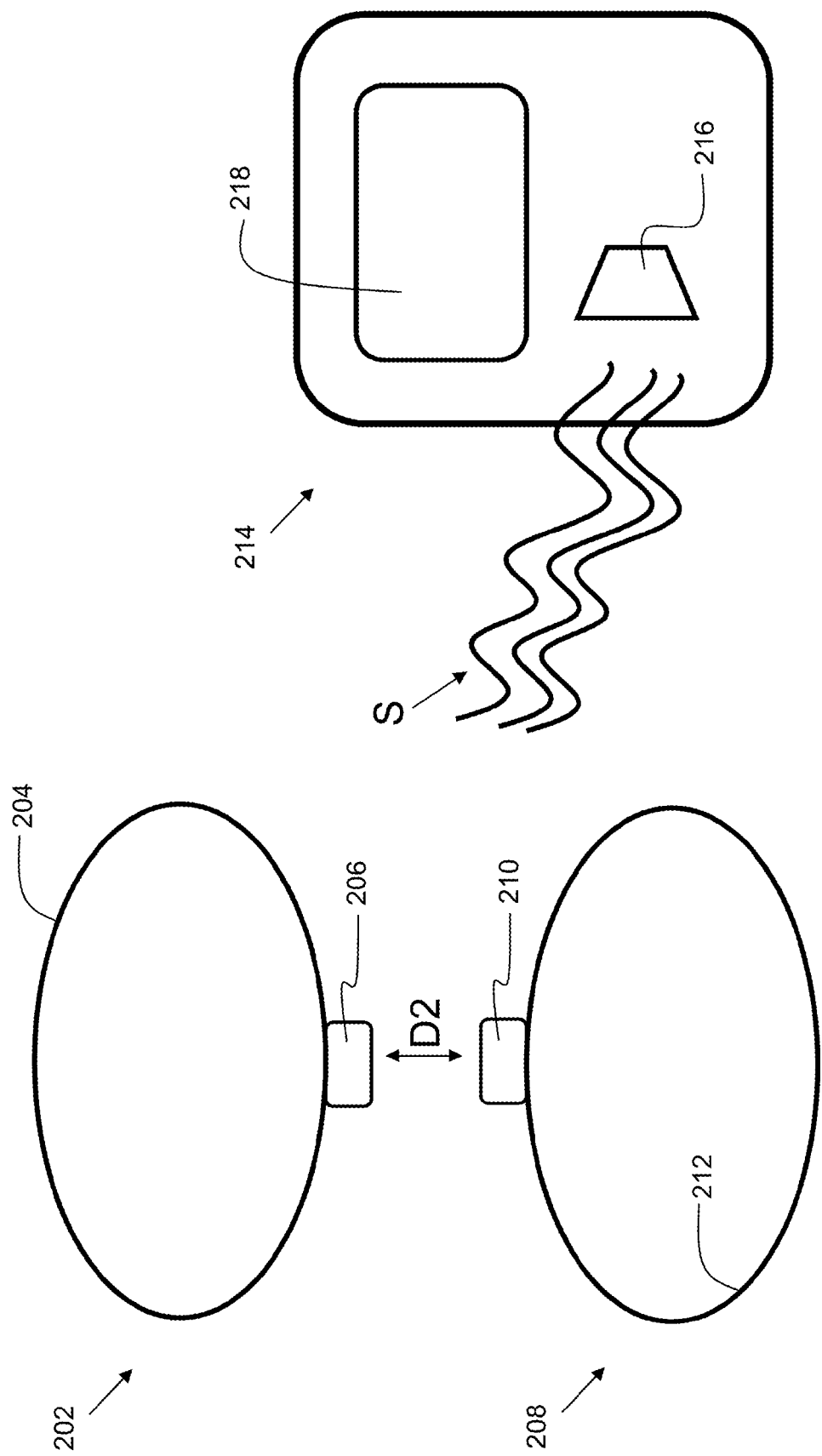
FIG. 3 shows a system with two relative position indicators and a sound module in an activated state.

FIG. 3 shows a system with two wearable relative position indicators and a sound module in an activated (proximal) state. As shown, the two WRPI housings are separated by a distance D2, where D2 is less than D1 (of FIG. 2). In embodiments, D1 may range from about 5 inches to about 8 inches, and D2 may range from about 1 inch to about 3 inches. During intercourse, as the two users vary their distance during thrusting motion, the proximity sensors in the respective housings (206 and 210) sense proximity, and send a signal to the sound module 214. In response to receiving the proximity indication, sound module 214 emits sound S from speaker 216. The sound is thus synchronized to the thrusting activity during sexual intercourse. In embodiments, the sound may be a bass note, drum sound, or other sound as specified by a user or randomly selected. During use, a first person may switch their WRPI to the "A" mode (see 108 of FIG. 1), and the second person then switches their WRPI to the "B" mode. In A mode, the WRPI transmits proximity information to the sound module. In B mode, the WRPI does not transmit proximity information to the sound module. Since only one WRPI need transmit the proximity information to the sound module, one user puts their WRPI in B mode, while the other user puts their WRPI in A mode, prior to use.

Figure 4:
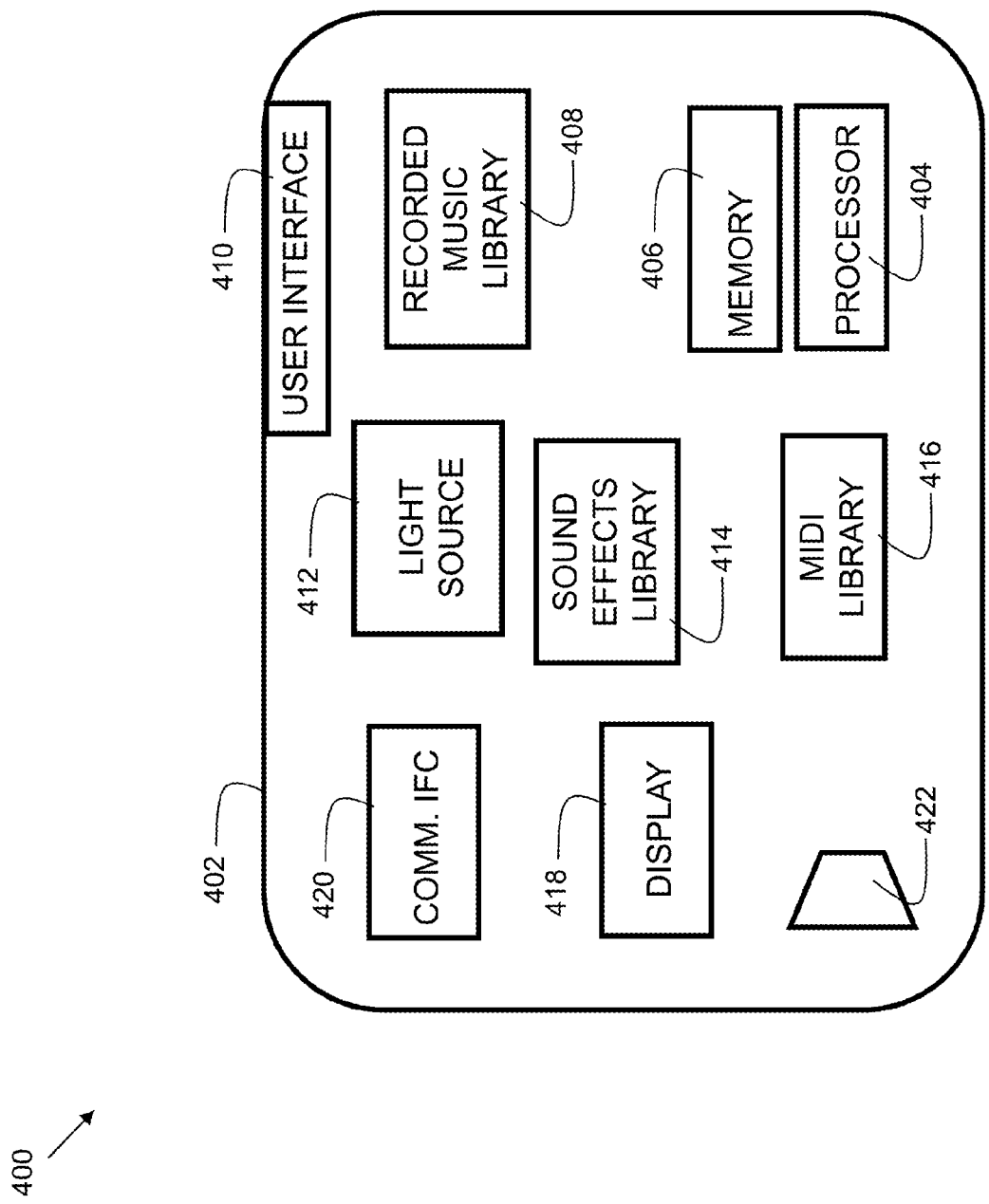
FIG. 4 shows a block diagram of a sound module in accordance with embodiments of the present invention.

FIG. 4 shows a block diagram of a sound module in accordance with embodiments of the present invention. The sound module 400 comprises housing 402 which houses a processor 404, which is coupled to memory 406. Memory 406 contains instructions, that when executed by the processor, perform the functions of the sound module 400. Sound module 400 further includes a speaker 422 for producing audible sounds. Sound module 400 further includes communication interface 420 for receiving proximity information from a WRPI during sexual intercourse. In embodiments, the communications interface 420 may include a Bluetooth™ interface, a frequency modulation (FM) radio, a WiFi (IEEE 802.11) interface, and/or an amplitude modulation (AM) radio. In some embodiments, the WRPI that is in A mode is paired with the sound module 400 via Bluetooth™, and the proximity information is transmitted from the WRPI that is in A mode to the sound module 400 via Bluetooth™. In other embodiments, an FM or AM signal may be used to transmit proximity information to the sound module. In some embodiments, the sound module may be a commercial off the shelf (COTS) item such as a tablet computer or smart phone that is running an application (app). The sound module 400 further includes a sound effects library 414 that includes multiple sound effects. In embodiments, the sound effects may be stored in a digital format such as PCM, MP3, OGG, or other suitable format. The sound effects may include sounds of duration ranging from about 200 milliseconds to 1 second. The sound effects may include bass notes, percussive sounds, whistles, and other musical instrument sounds. The sound effects library 414 may be stored in a non-volatile memory such as flash. The sound module 400 may further include a MIDI library 416 which is also stored in a non-volatile memory such as flash. In some embodiments, the sound module 400 may detect a tempo of the sexual intercourse based on a proximity signal, and render music from the MIDI library at the approximate tempo of the sexual intercourse. The sound module 400 may further include a recorded music library 408 which is also stored in a non-volatile memory such as flash. The recorded music library may be stored in a format such as MP3. The recorded music library may further include a table indicating beats-per-minute (BPM) of each song in the recorded music library 408. In some embodiments, the sound module 400 may detect a tempo of the sexual intercourse based on a proximity signal, and render music from the recorded music library that has the approximate tempo of the sexual intercourse. The sound module 400 may further include a display 418 and user interface 410. In some embodiments, the display 418 may be a touch screen that can also implement user interface 410. The user interface may provide screens for configuring the system. The sound module 400 may further include a light source 412. The light source may be a strobe light or other light source such as an LED (light emitting diode) light source. The light source may be activated to flash based on a proximity signal. In some embodiments, the display may serve as the light source. In such embodiments, the display may flash white based on a proximity signal indicating a close proximity (e.g. D2 from FIG. 3), and then go black based on a proximity signal indicating a far proximity (e.g. D1 from FIG. 2). In some embodiments, the sound module may utilize a WiFi connection from communication interface 420 to access an external sound library (e.g. via the Internet) to allow access to new songs and sound effects. The sound module 400 may use its internal sound libraries (408, 414, and/or 416) when operating in a stand-alone mode, where no Internet is available, such as when camping, for example.

Figure 5:
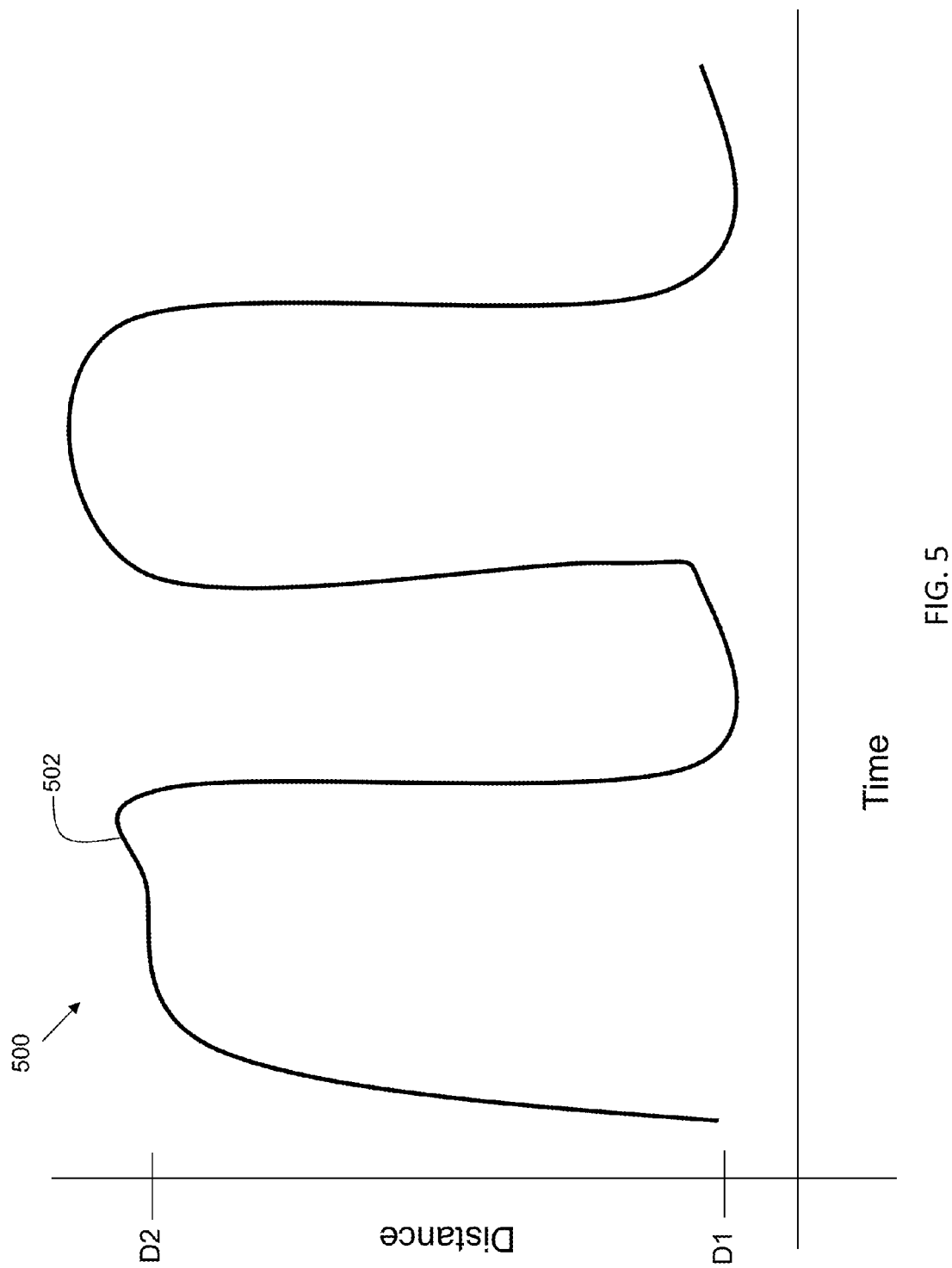
FIG. 5 shows an example of raw sensor data.

FIG. 5 shows an example of raw sensor data. Graph 500 shows signal 502 which varies in relation to the distance between two WRPI worn during sexual intercourse between two people. The signal 502 may range from a low value corresponding to a far distance D1, and then increase to a high value corresponding to a close distance D2. Raw signal 502 may then be further processed to derive a digital proximity signal as described in FIG. 6.

Figure 6:
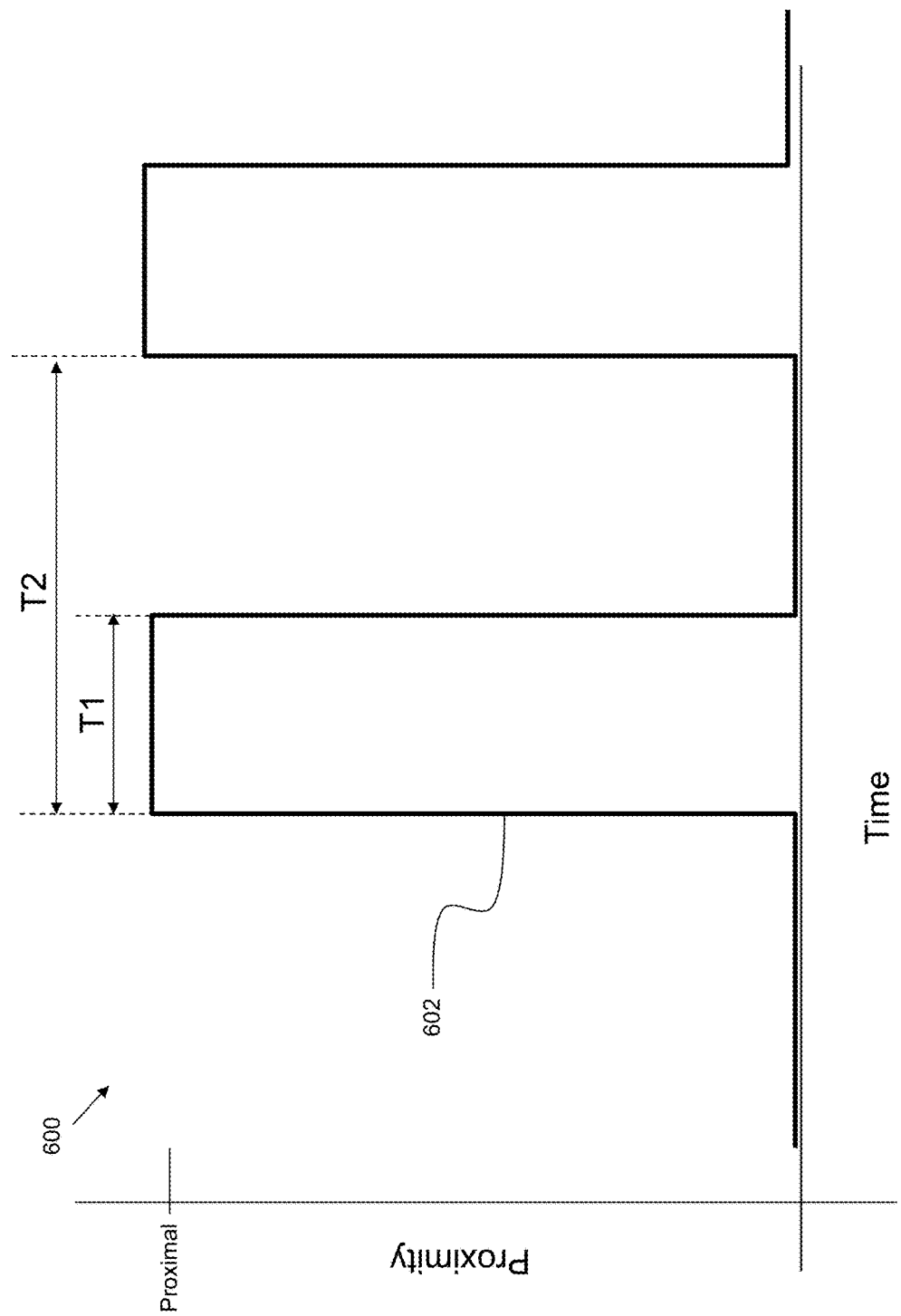
FIG. 6 shows an example of a proximity signal based on raw sensor data.

FIG. 6 shows a graph 600 of a proximity signal 602 based on raw sensor data. The proximity signal may be derived from the raw sensor data by inverting it and clamping the levels to a high and low level based on the inverted raw sensor data signal. Thus, the proximity signal 602 may be a digital signal that is at a logical low level when the distance between the two WRPI exceeds a predetermined distance (e.g. 4 inches), and is at a logical high level when the two WRPI are at or within the predetermined distance (e.g. 4 inches). The high level indicates a proximal state. The proximal state is a state when the two WRPI are at or within the predetermined distance (e.g. 4 inches). The non-proximal state is a state when the two WRPI are located at a distance from each other that exceeds the predetermined distance (e.g. 4 inches). The signal 602 has a proximity duration defined by time T1. Time T1 is a measure of how long the two WRPI are at or within the predetermined distance. The signal 602 has a proximity frequency that is a function of time T2. Time T2 is a measure of time between two occurrences of a proximal state of the two WRPI. Times T1 and T2 can be used to obtain parameters about the sexual intercourse. In embodiments, the sound module (400 of FIG. 4) may track time T2 over a plurality of samples (e.g. 10 samples), and derive an average tempo corresponding to the thrusting of people during sexual intercourse. Music and/or sound is then selected based on the detected tempo. The time T1 may be used to detect a completion phase. At the end of a sexual intercourse session, the two WRPI may be in a proximal state for a prolonged period (e.g. more than four seconds). This extended time T1 may be used to signal the end of the sexual activity. The sound module 400 may play a different sound or music based on the extended time T1. In this way, the users can experience a different sound near the climax of their sexual intercourse. For example, the users may hear a thumping bass drum synchronized to the thrusting during the sexual intercourse. At the ending of the sexual intercourse, if the two users keep their bodies close together such that the two WRPI are kept within range, a new sound, such as a choir, trumpet, applause, or other "ending" sound effect can be played.

Figure 7:
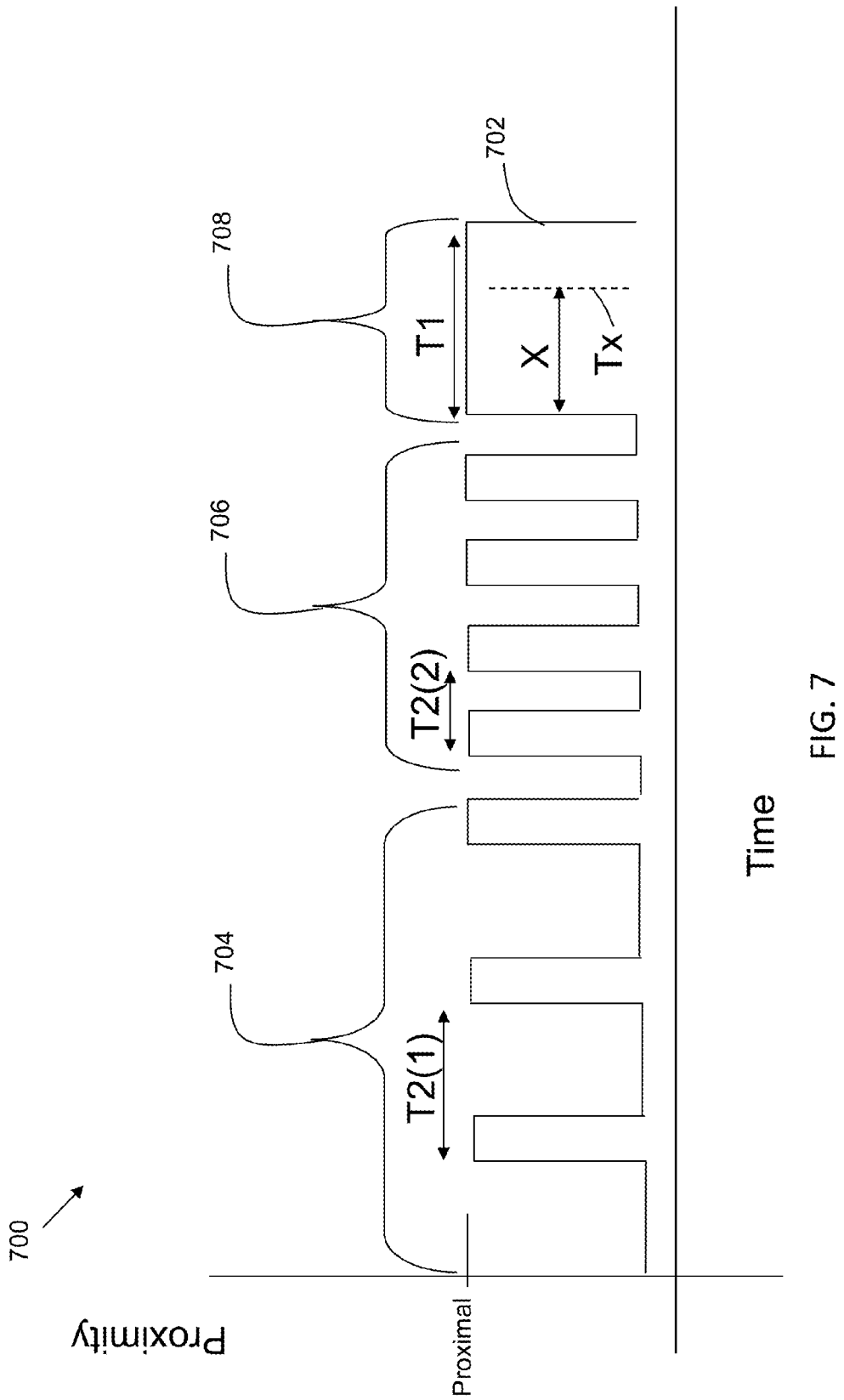
FIG. 7 shows an example of a proximity signal during sexual intercourse.

FIG. 7 shows a graph 700 of a digital proximity signal 702 during sexual intercourse. During a first phase of sexual intercourse, indicated as 704, there is a detected tempo based on time T2(1). The detecting of a tempo is based on the frequency of transition to the proximal state of the digital proximity signal 702. During a second phase of sexual intercourse, indicated as 706, there is a detected tempo based on time T2(2). Since T2(2) is less than T2(1), this indicates an increase in tempo. Upon detecting an increase in tempo, the sound module 400 may render a sound at a faster tempo to remain synchronized with the thrusting of the users. Alternatively, the sound module may adjust the playback tempo of a MIDI file, or alternatively, select a new recorded music song with a tempo approximately close to the detected tempo during phase 706. Alternatively, the tempo may be a multiple of the detected tempo. For example, if the detected tempo during phase 706 is 60 thrusts per minute, then the selected song may have a tempo of about 120 beats per minute. During a final phase of sexual intercourse, indicated as phase 708, the time T1 exceeds predetermined threshold X. For example, X may be four seconds. At time Tx, the sound module may play an ending sound, such as a choir, trumpet, applause, or other "ending" sound effect to coincide with the end of the sexual intercourse.

Figure 8:
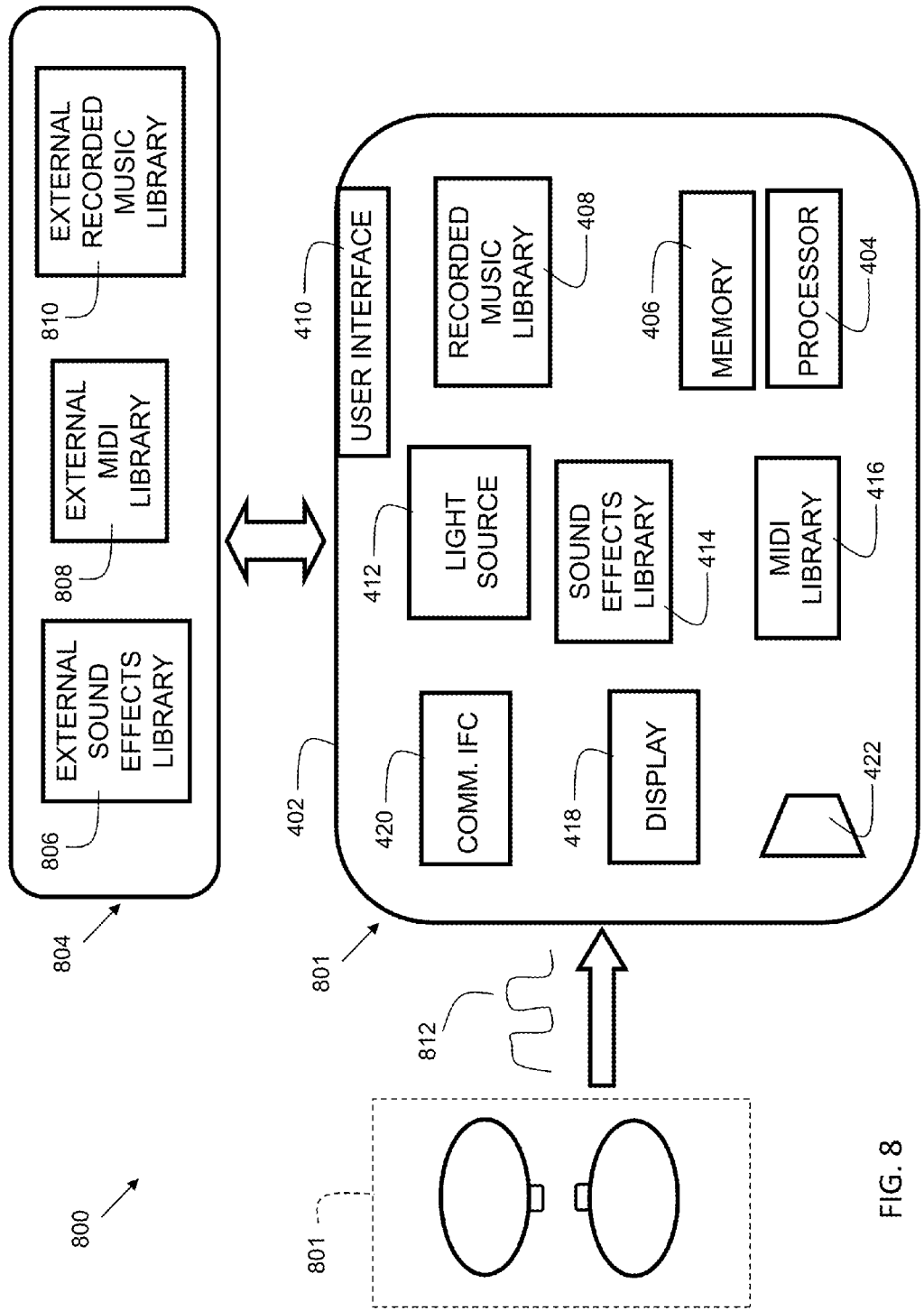
FIG. 8 shows a block diagram of a system in accordance with alternative embodiments of the present invention.

FIG. 8 shows a block diagram of a system 800 in accordance with alternative embodiments of the present invention. A pair of WRPIs, indicated as 801 are worn by two users engaging in sexual intercourse. The thrusting motion of the two users creates raw sensor data signal 812 which is transmitted by the WRPI in A mode to the sound module 801. The sound module 801 may process the raw sensor data signal 812 to create a proximity signal. Alternatively, the WRPI may create the proximity signal and send it directly to the sound module 801. The sound module 801 renders sounds and/or lights corresponding to the proximity signal. Optionally, the sound module 801 may interface with an external sound library 804. In embodiments, the external sound library 804 may be accessed via the Internet. The external sound library contains an external sound effects library, external MIDI library, and/or an external recorded music library. In this way, the sound module can be updated with new songs and sounds periodically. In embodiments, the new songs and sounds are transferred from the external sound library 804 and stored in memory 406 within the sound module 801.

Figure 9:
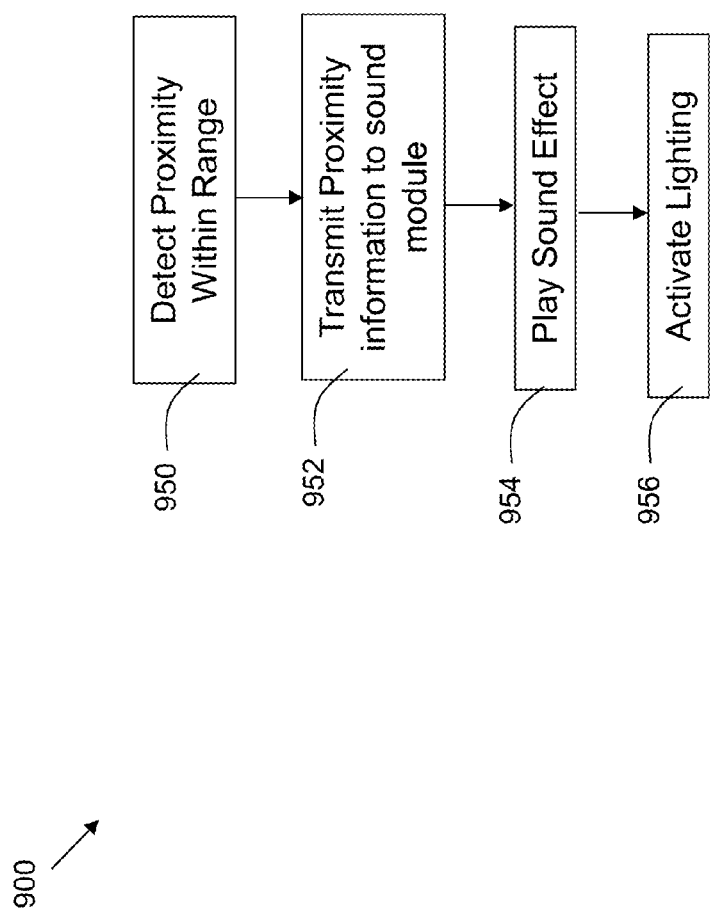
FIG. 9 is a flowchart indicating process steps for a method in accordance with embodiments of the present invention.

FIG. 9 is a flowchart 900 indicating process steps for a method in accordance with embodiments of the present invention. In process step 900, the proximity between the two WRPI is determined to be less than or equal to a predetermined distance. In process step 952, proximity information is transmitted from one of the WRPI to the sound module. The transmission is preferably wireless, and may be performed via AM radio, FM radio, or Bluetooth™, for example. In embodiments, the transmission includes a representation of raw sensor data. In other embodiments, the transmission may include a digital proximity signal that is based on raw sensor data. In process step 954, the sound module plays a sound effect corresponding to the proximal state of the two WRPI. In process step 956, optionally, lighting such as a strobe is activated, corresponding to the proximal state.

Figure 10:
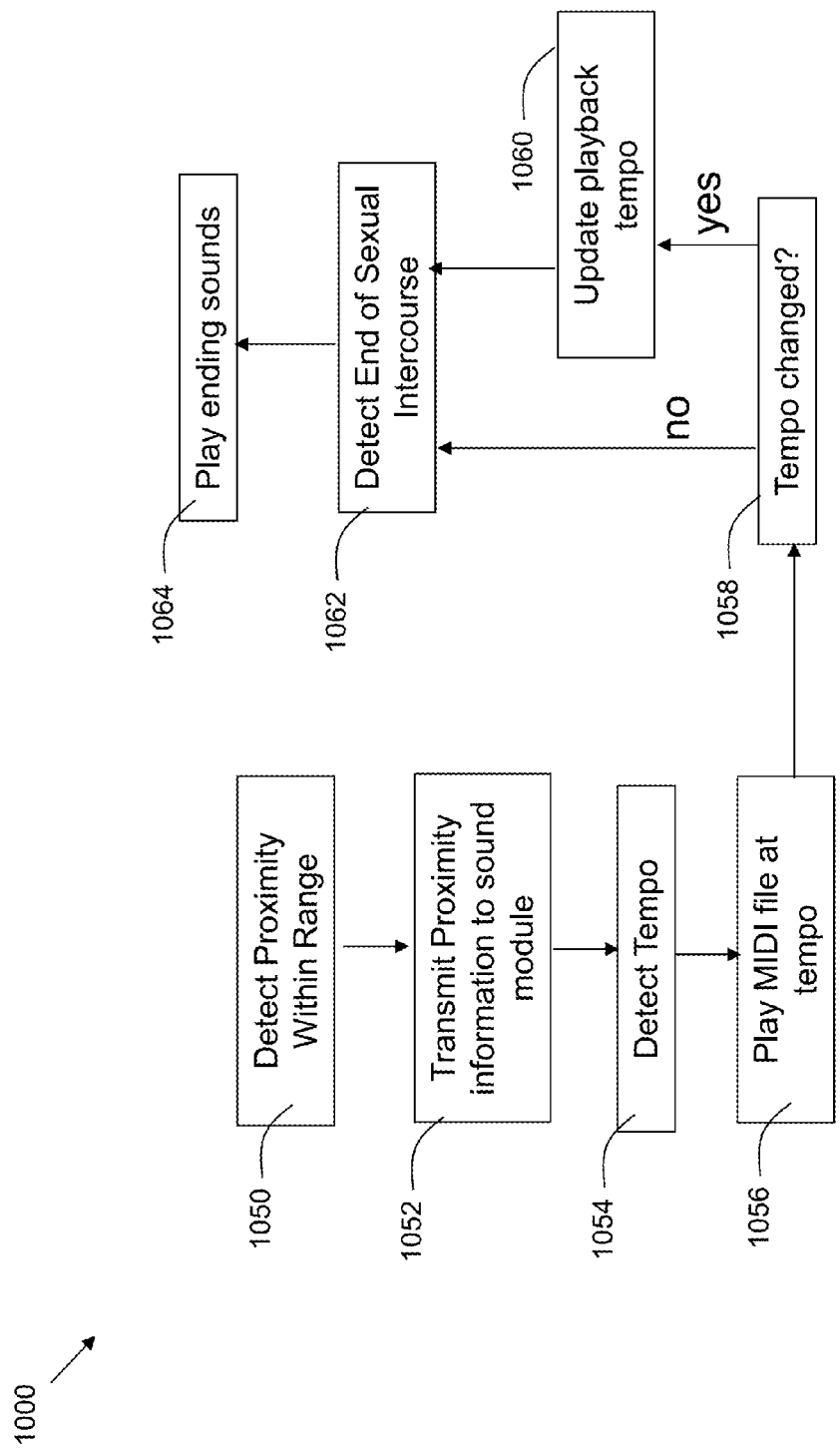
FIG. 10 is a flowchart indicating process steps for a method in accordance with additional embodiments of the present invention.

FIG. 10 is a flowchart indicating process steps for a method in accordance with additional embodiments of the present invention. In process step 1000, the proximity between the two WRPI is determined to be less than or equal to a predetermined distance. In process step 1052, proximity information is transmitted from one of the WRPI to the sound module. The transmission is preferably wireless, and may be performed via AM radio, FM radio, or Bluetooth™, for example. In embodiments, the transmission includes a representation of raw sensor data. In other embodiments, the transmission may include a digital proximity signal that is based on raw sensor data. In process step 1054, the sound module detects a tempo corresponding to the entry and exit times of the proximal state of the two WRPI. In process step 1056, a MIDI file is played at a tempo corresponding to the detected tempo. In embodiments, the tempo of the MIDI file playback may be a multiple of the detected tempo. In process step 1058, the sound module periodically monitors for a change in detected tempo. If yes, then the tempo of the MIDI file playback is updated in process step 1060. If no, then the process continues to process step 1062 of detecting an end to the sexual intercourse (such as phase 708 of FIG. 7). Upon detecting the end of sexual intercourse, the sound module may optionally play an ending sound in process step 1064.

Figure 11:
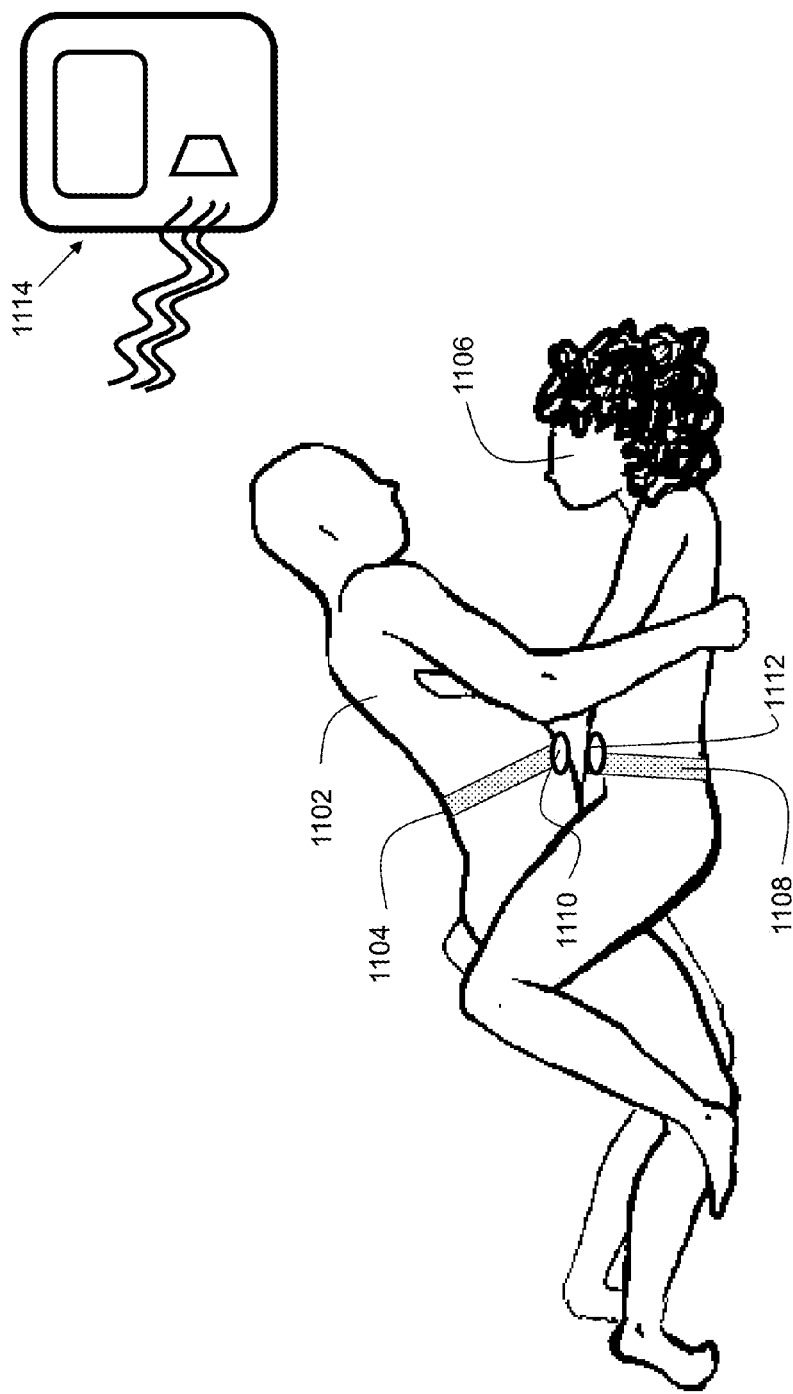
FIG. 11 illustrates the use of wearable sensors in a front-to-front arrangement.

FIG. 11 illustrates the use of wearable sensors in a front-to-front arrangement. A first person 1102 wears a WRPI 1104 having housing 1110 positioned in front of him. A second person 1106 wears WRPI 1108 having housing 1112 positioned in front of her. The housings are oriented such that the distance between the housing 1110 and housing 1112 changes proportionally to the thrusting motion occurring during sexual intercourse. The sound module 1114, typically located in the same room as the first person 1102 and second person 1106, renders sound and/or light that is synchronized to the thrusting motions of person 1102 and/or person 1106.

Figure 12:
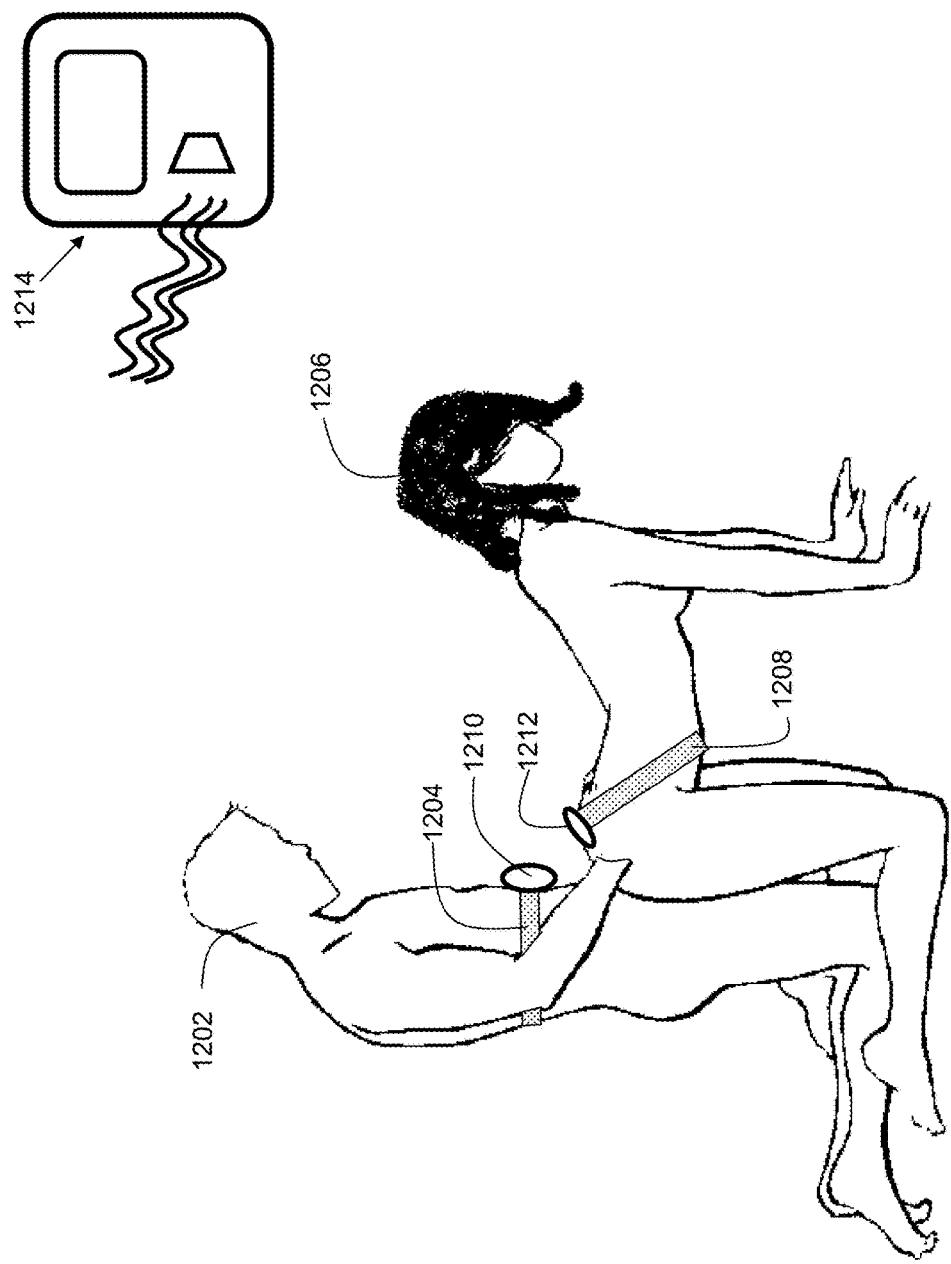
FIG. 12 illustrates the use of wearable sensors in a front-to-back arrangement.

FIG. 12 illustrates the use of wearable sensors in a front-to-back arrangement. A first person 1202 wears a WRPI 1204 having housing 1210 positioned in front of him. A second person 1206 wears WRPI 1208 having housing 1212 positioned behind her. The housings are oriented such that the distance between the housing 1210 and housing 1212 changes proportionally to the thrusting motion occurring during sexual intercourse. The sound module 1214, typically located in the same room as the first person 1202 and second person 1206, renders sound and/or light that is synchronized to the thrusting motions of person 1202 and/or person 1206. In some embodiments, the WRPI may be a complementary pair. One of the WRPI may include a sensor, while the other WRPI includes a signal generation mechanism to generate a signal that is received by the sensor. In some embodiments, the signal generation mechanism may include one or more magnets that emit an electromagnetic wave detected by the other WRPI. In some embodiments, one WRPI may include a RF receiver and the other WRPI may include an RF transmitter.

Figure 13:
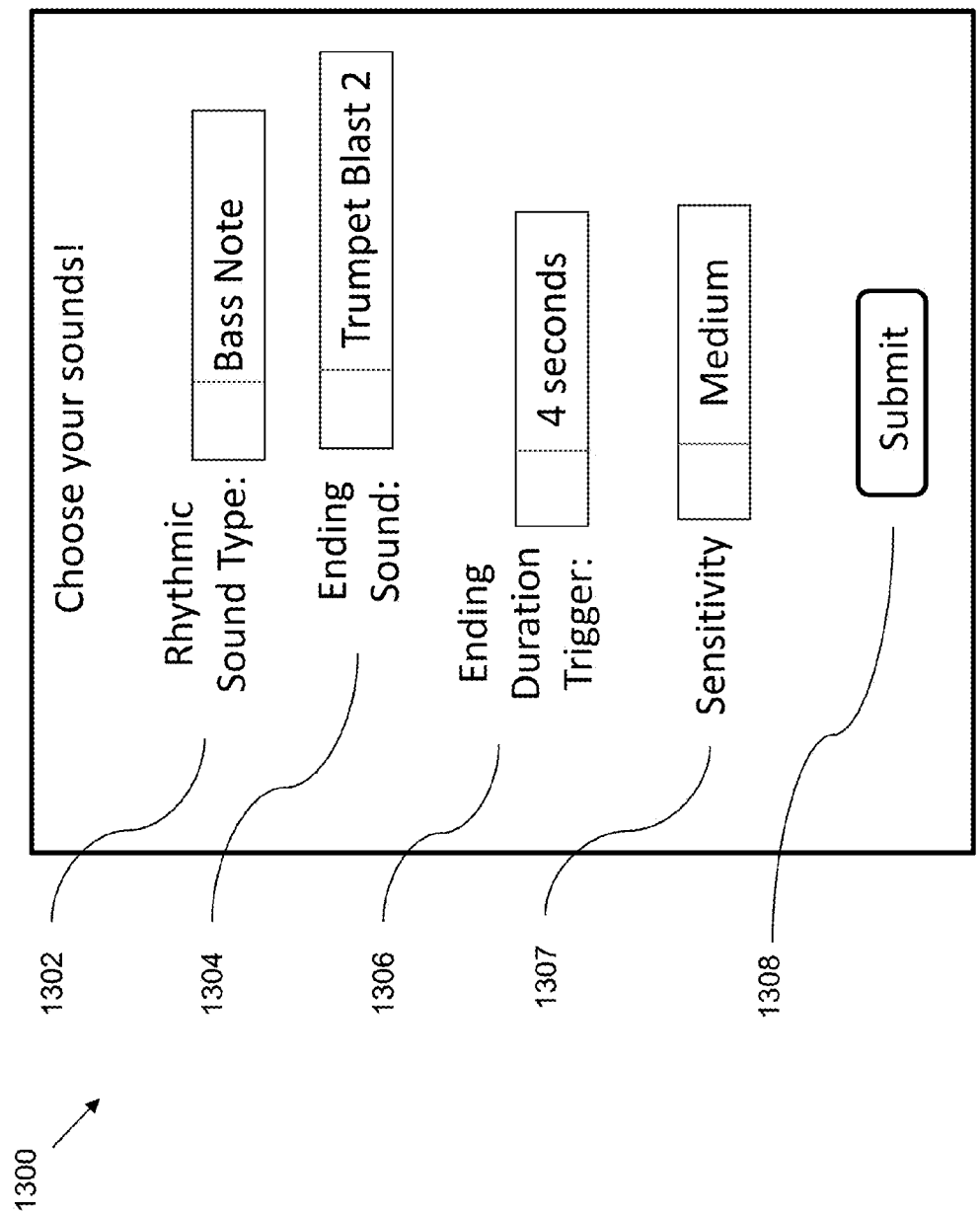
FIG. 13 is an example user interface for system setup.

FIG. 13 is an example user interface 1300 for system setup. User interface 1300 provides a field 1302 for selection of a rhythmic sound type. The rhythmic sound type is rendered or output as a result of detecting a proximal state of the two WRPI. Embodiments may include rhythmic sound types such as bass notes, drum sounds, chimes, glass breaking, and/or other sound effects. User interface 1300 provides a field 1304 for selection of an ending sound. The ending sound is rendered or output upon detecting an end of sexual intercourse (such as phase 708 of FIG. 7). Embodiments may include ending sounds such as trumpet sounds, choir sounds, applause, and/or other sound effects. User interface 1300 includes a sensitivity field 1307 that controls the sensitivity of the proximity sensors. The setting affects the distance at which the two WRPI are considered to be in the proximal state. This setting can be adjusted by the users to accommodate their style and range of motion during sexual intercourse. User interface 1300 includes a Submit button 1308 for making the desired options take effect. In embodiments, user interface 1300 is rendered on the display (418 of FIG. 4) of the sound module 400.

Figure 14:
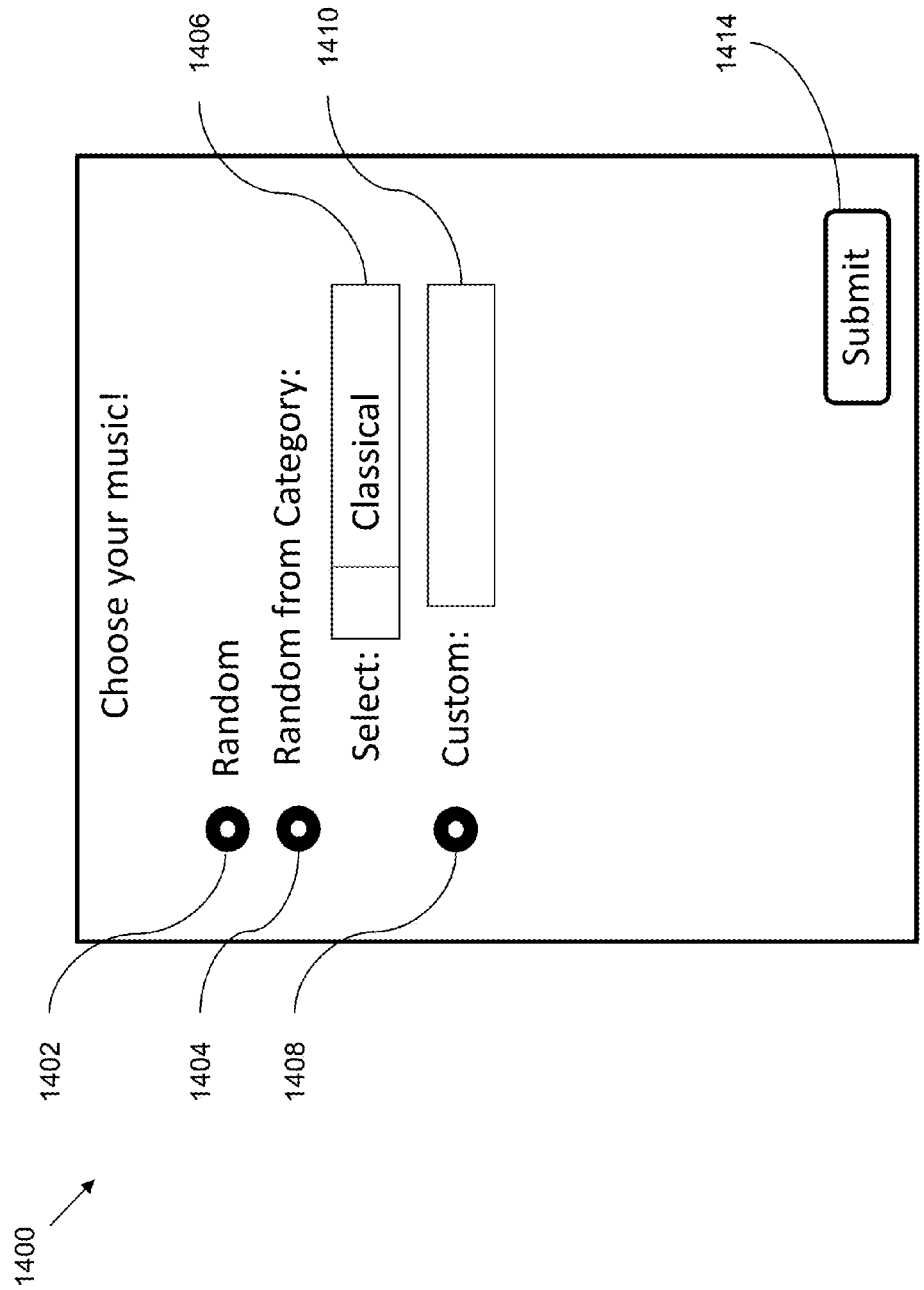
FIG. 14 is another example user interface for system setup.

FIG. 14 is another example user interface 1400 for system setup. User interface 400 provides radio button 1402 to select random music to be played during the sexual intercourse. User interface 400 provides radio button 1404 to select random music from a specific category to be played during the sexual intercourse. The category of music (e.g. genre) may be selected in field 1406. User interface 1400 provides radio button 1408 to enable a custom music selection that is entered in field 1410. In embodiments, the custom music selection may be a particular song, album, artist, or playlist. User interface 1400 includes a Submit button 1414 for making the desired options take effect. In embodiments, user interface 1400 is rendered on the display (418 of FIG. 4) of the sound module 400.

As can now be appreciated, embodiments of the present invention provide a system, apparatus, and method for enabling increased excitement and intimacy during the important activity of sexual intercourse. Thus, the experience of sexual intercourse is further enhanced by the audio and visual stimulation that is synchronized to the thrusting activity of the sexual intercourse.

While the invention has been particularly shown and described in conjunction with exemplary embodiments, it will be appreciated that variations and modifications will occur to those skilled in the art. For example, although some of the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with the present invention. Furthermore, the methods according to the present invention may be implemented in association with the formation and/or processing of structures illustrated and described herein as well as in association with other structures not illustrated. Moreover, in particular regard to the various functions performed by the above described components (assemblies, devices, circuits, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of the invention.

What is claimed is:

1. A system for producing output synchronized to sexual intercourse motion, comprising:
   a first wearable relative position indicator configured to be worn on a first person;
   a second wearable relative position indicator configured to be worn on a second person;
   a sound module disposed to:
      receive sensor data from the first wearable relative position indicator,
      convert the sensor data into a proximity signal;
      play, based on the proximity signal, a first sound effect during sexual intercourse between the first person and second person; and
      play a second sound effect upon completion of sexual intercourse between the first person and second person.

2. The system of claim 1, wherein the sound module further comprises a light source.

3. The system of claim 1, wherein the sound module further comprises a MIDI file library.

4. The system of claim 1, wherein the sound module further comprises a recorded song library.

5. The system of claim 1, wherein the sound module further comprises a sound effects library.

6. The system of claim 1, wherein the sound module further comprises a network interface configured to access an external sound library via an Internet.

7. The system of claim 1, wherein each wearable relative position indicator comprises a proximity sensor disposed within a housing, wherein the housing is affixed to a belt.

8. The system of claim 1, wherein the sound module is an application running on a computing device.

9. A method for producing stimulus that is synchronized to sexual intercourse motion, comprising:
   transmitting sensor data indicative of distance between a first wearable relative position indicator and a second wearable relative position indicator;
   converting the sensor data into a digital proximity signal comprising a proximal state and a non-proximal state;
   emitting a first sound effect when the digital proximity signal indicates a proximal state; and
   detecting an end of sexual intercourse based on the digital proximity signal indicating a proximal state for a period of time exceeding a predetermined threshold.

10. The method of claim 9, further comprising emitting light from a light source when the digital proximity signal indicates a proximal state.

11. The method of claim 9, further comprising emitting a second sound effect upon detecting the end of sexual intercourse.

12. The method of claim 9, wherein the emitting the first sound effect comprises emitting the first sound effect through an application running on a computing device.

13. A method for producing stimulus that is synchronized to sexual intercourse motion, comprising:
   transmitting sensor data indicative of distance between a first wearable relative position indicator and a second wearable relative position indicator;
   converting the sensor data into a digital proximity signal comprising a proximal state and a non-proximal state;
   detecting a first tempo based on a frequency of transition to the proximal state of the digital proximity signal;
   playing first music corresponding to the detected first tempo;
   detecting a second tempo based on a change in the frequency of transition to the proximal state of the digital proximity signal; and
   playing second music corresponding to the detected second tempo.

14. The method of claim 13, wherein playing the first music comprises playing a MIDI file at a playback tempo matching the detected first tempo.

15. The method of claim 13, wherein playing the first music comprises playing a recorded music file having a recorded tempo corresponding to the detected first tempo.

16. The method of claim 13, wherein the first music and the second music is played through an application running on a computing device.

17. The method of claim 13, further comprising emitting light from a light source when the digital proximity signal indicates a proximal state.

* * * * *